(12) United States Patent
Schlitzer et al.

(10) Patent No.: US 7,025,958 B2
(45) Date of Patent: Apr. 11, 2006

(54) **USE OF AMIDOAMINES TO TREAT OR PREVENT *ACANTHAMOEBA* AND FUNGAL INFECTIONS**

(75) Inventors: Ronald L. Schlitzer, Fort Worth, TX (US); Nissanke L. Dassanayake, Arlington, TX (US); Ruth Ann Rosenthal, Alvarado, TX (US); Sally L. Buck, Grand Prairie, TX (US)

(73) Assignee: Alcon, Inc., Hunenberg (CH)

( * ) Notice: Subject to any disclaimer, the term of this patent is extended or adjusted under 35 U.S.C. 154(b) by 119 days.

(21) Appl. No.: 10/415,836

(22) PCT Filed: Nov. 27, 2001

(86) PCT No.: PCT/US01/44408
§ 371 (c)(1),
(2), (4) Date: Apr. 30, 2003

(87) PCT Pub. No.: WO02/49633
PCT Pub. Date: Jun. 27, 2002

(65) Prior Publication Data
US 2004/0058924 A1 Mar. 25, 2004

Related U.S. Application Data

(60) Provisional application No. 60/257,572, filed on Dec. 20, 2000.

(30) Foreign Application Priority Data
Dec. 20, 2000 (US) .......................................... 60257572

(51) Int. Cl.
*A61K 31/74* (2006.01)

(52) U.S. Cl. ........................ 424/78.04; 554/51; 554/64; 514/839; 514/840

(58) Field of Classification Search .................. 554/51, 554/64; 514/839, 840; 424/78.04
See application file for complete search history.

(56) References Cited

U.S. PATENT DOCUMENTS 5,393,491 A * 2/1995 Dassanayake et al. ........ 422/28
5,573,726 A * 11/1996 Dassanayake et al. ........ 422/28
5,631,005 A * 5/1997 Dassanayake et al. ... 424/78.04

FOREIGN PATENT DOCUMENTS

WO     WO 00/18386     4/2000

OTHER PUBLICATIONS

Rosenthal et al., CLAO Journal, vol. 25, No. 4, pp. 213–217, Oct. 1999.*
Rosenthal et al., CLAO Journal, vol. 26, No. 3, pp. 120–126, 06/872000.*
Wright, et al., *Acanthamoeba Keratitis Sucessfully Treated Medically*, British Journal of Ophthalmology, vol. 69, pp. 778–782 (1985).

Seal, et al., *Successful Medical Therapy of Acanthamoeba Keratitis With Topical Chlorhexidine and Propamidine*, Eye, vol. 10, pp. 413–421 (1996).
Perrine, et al., *Amoebicidal Efficiencies of Various Diamidines Against Two Strains of Acanthamoeba Polyhaga*, Antimicrobial Agents and Chemotherapy, vol. 39, No. 2, pp. 339–342 (1995).
Osato, et al. *Cysticidal Activity of 21 Antimicrobial Agents Against 11 Corneal Isolates of Acanthamoeba*, Invest. Ophthalmology Visual Science—Immunology & Microbiology—Monday AM Poster Presentation, vol. 29, p. 40 (1988).
Murdoch, et al., *Acanthamoeba Keratitis in New Zealand, Including Two Cases with In Vivo Resistance to Polyhexamethylene Biguanide*, Australian and New Zealand Journal of Ophthalmology, vol. 26, pp. 231–236 (1998).
Lindquist, et al., *Clinical Signs and Medical Therapy of Early Acanthamoeba Keratitis*, Arch. Ophthalmol, vol. 106, pp. 73–77 (1988).
Lindquist, *Treatment of Acanthamoeba Keratitis*, Cornea, vol. 17, No. 1, pp. 11–16 (1998).
Larkin, et al., *Treatment of Acanthamoeba Keratitis with Polyhexamethylene Biguanide*, Ophthalmology, vol. 99, No. 2, pp. 185–191 (1992).
Kilvington, et al., *Acanthamoeba: Biology, Ecology and Human Disease*, Reviews in Medical Microbiology, vol. 5, No. 1, pp. 12–20 (1994).
Ishibashi, et al., *Oral Itraconazole and Topical Miconazole with Debridement for Acanthamoeba Keratitis*, American Journal of Ophthalmology, vol. 109, No. 2, pp. 121–126 (1990).
Hay, et al., *Drug Resistance and Acanthamoeba Keratitis: The Quest for Alternative Antiprotozoal Chemotherapy*, Eye, vol. 8, pp. 555–563 (1994).
Gray, et al., *Acanthamoeba Keratitis: A Sobering Case and a Promising New Treatment*, Australian and New Zealand Journal of Ophthalmology, vol. 22, No. 1, pp. 73–76 (1994).
Duguid, et al., *Outcome of Acanthamoeba Keratitis Treated with Polyhexamethyl Biguanide and Propamidine*, Ophthalmology, vol. 104, No. 10, pp. 1587–1592 (1997).
Van Duzee, et al., *The Activity of a Multi–Purpose Solution Against Acanthamoeba*, Optician, vol. 217, No. 5700, pp. 34–35 (1999).
Brasseur, et al., *Successful Treatment of Acanthamoeba Keratitis by Hexamidine*, Cornea, vol. 13, No. 5, pp. 459–462 (1994).
Buck, et al., *Amoebicidal Activity of a Preserved Contact Lens Multipurpose Distinfecting Solution Compared to a Disinfection/Neutralisation Peroxide System*, Contact Lens and Anterior Eye, vol. 21, No. 3, p. 81–84 (1998).

(Continued)

*Primary Examiner*—Deborah D. Carr
(74) *Attorney, Agent, or Firm*—Gregg C. Brown

(57) ABSTRACT

The use of amidoamines to treat or prevent infections attributable to *Acanthamoeba* and fungi is described. The amidoamines are highly effective against both *Acanthamoeba* and fungi, and are less toxic to delicate tissues that may become infected with these types of microorganisms (e.g., the cornea).

11 Claims, No Drawings

OTHER PUBLICATIONS

Buck, et al., *A Quantitative Method to Evaluate Neutralizer Toxicity Against Acanthamoeba Castallanii*, Applied and Environmental Microbiology, vol. 62, No. 9, pp. 3521–3526 (1996).

Burger, et al., *Killing Acanthamoebae with Polyaminopropyl Biguanide: Quantitation and Kinetics*, Antimicrobial Agents and Chemotherapy, vol. 38, No. 4, pp. 886–888 (1994).

Cohen, et al., *Medical and Surgical Treatment of Acanthamoeba Keratitis*, American Journal of Ophthalmology, vol. 103, No. 5, pp. 615–625 (1987).

Kilvington, et al., *A Comparisoin of Cyst Age and Assay Method of the Efficacy of Contact LEns Disinfectants Against Acanthamoeba*, British Journal of Ophthalmology, vol. 85, pp. 336–340 (2001).

Rosenthal, et al., *Broad Spectrum Antimicrobial Activity of a New Multi–Purpose Disinfecting Solution*, The CLAO Journal, vol. 26, No. 3, pp. 120–126 (Jul. 2000).

Rosenthal, et al., *Antimicrobial Comparison of a New Multi–Purpose Disinfecting Solution to a 3 Hydrogen Peroxide System*, The CLAO Journal, Vo. 25, No. 4, pp. 213–217 (Oct. 1999).

Claerhout, et al., *Acanthamoeba Keratitis: A Review*; Bull. Soc. Belge Ophthalmol., vol. 274; pp. 71–82 (1999).

Korirukvongs, et al., *Treatment of Acanthameoba Keratitis with Chlorhexidine*, Ophthalmology, vol. 6, No. 4, pp. 798–802 (Apr. 1999).

Tien, et al., *Treatment of Acanthamoeba Keratitis Combined With Fungal INfection with Polyhexamethylene Biguanide*, Kaohsiung Journal Medical Science, vol. 15, pp. 665–673 (1999).

Gatti, et al., *In Vitro Effectiveness of Povidone–Iodine on Acanthamoeba Isolates from Human Cornea*, Antimicrobial Agents and Chemotherapy, vol. 42, No. 9, pp. 2232–2234 (Sep. 1998).

Illingworth, et al., *Acanthamoeba Keratitis*, Survey of Ophthalmology, vol. 42, No. 6, pp. 493–508, (Jun. 1998).

Azuara–Blanco, et al., *Successful Medical Treatment of Acanthamoeba Keratitis*, International Ophthalmology, vol. 21, pp. 223–227 (1998).

Hargrave, et al., *Results of a Trial of Combined Propamidine Isethionate and Neomycin Therapy for Acanthamoebas Keratitis*, Ophthalmology, vol. 106, No. 5, pp. 952–957 (May 1999).

Amoils, et al., *Acanthamoeba Keratitis with Live Isolates Treated with Cryosurgery and Fluconazole*, American Journal of Ophthalmology, vol. 127, No. 6, pp. 718–720 (Jun. 1999).

Guerrero, et al., *Queratitis Por Acanthamoeba: A Proposito De Un Caso Bilateral*, Farm Hospital, vol. 22, No. 5, pp. 253–255 (Feb. 1998).

Park, et al., *The Role of Topical Coricosteroids in the Management of Acanthamoeba Keratitis*, Cornea, vol. 16, No. 3, pp. 277–283 (1997).

Chung, et al., *Fungal Keratitis After Laser In Situ Keratomileusis: A Case Report*, Cornea, vol. 19, No. 2; pp. 236–237 (2000).

Rodriguez–Ares, et al., *Acremonium K eratitis in a Patient with Herpetifc Neurotrophic Corneal Disease*, Acta Ophthalmologica Scandinavica, vol. 78; pp. 107–109; (2000).

Rahman, et al., *Trial of Chlorhexidine Gluconate for Fungal Corneal Ulcers*, Ophthalmic Epidemiology, vol. 4, No. 3, pp. 141–149 (1997).

Muzyczko, et al., *Fatty Amidoamine Derivatives: N,N–Dimethyl–N–(3–alkylamidopropyl)amines and Their Salts*, The Jouranl of the American Oil Chemists' Society, vol. 45, No. 11, pp. 720–725, (Nov. 1968).

Kilvington, *Reducing the Risk of Microbial Keratitis in Soft Contact Lens Wearers*, Optician—Contact Lens Monthly, vol. 217, pp. 28–31 (Aug. 1996).

Rahman, et al., *Randomized Trial of 0.2*

Chlorhexidine Gluconate and 2.5

Natamycin for Fungal Keratitis in Bangladesh, British Journal of Ophthalmology, vol. 82 (1998) pp. 919–925.

\* cited by examiner

USE OF AMIDOAMINES TO TREAT OR PREVENT *ACANTHAMOEBA* AND FUNGAL INFECTIONS

This application claims priority from International Patent Application No. PCT/US01/44408 filed on Nov. 27, 2001, which claims priority from U.S. Provisional Application Ser. No. 60/257,572, filed on Dec. 20, 2000.

BACKGROUND OF THE INVENTION

The present invention is directed to the use of certain amidoamines to treat or prevent infections attributable to *Acanthamoeba*, fungi or combinations of these two types of microorganisms. The invention is particularly directed to the use of the amidoamines described herein to treat or prevent infections of the eye, ear, nose or throat. The pharmaceutical compositions and methods of treatment described herein are also useful in the topical treatment of dermatological infections.

The compositions of the present invention are particularly useful in treating or preventing ophthalmic infections, especially infections of the cornea. Infections of the cornea frequently lead to a serious inflammatory condition known as "keratitis". If such infections are left untreated, or if the selected therapy proves to be ineffective, *Acanthamoeba* and fungal infections of the cornea can lead to a rapid destruction of corneal tissues and, ultimately a loss of vision in the affected eye(s).

Various types of agents are currently utilized to treat *Acanthamoeba* infections. The agents utilized include cationic antiseptics, such as chlorhexidine and polyhexamethylene biguanide ("PHMB"); aromatic diamides, such as propamidine isethionate; and aminoglycoside antibiotics, such as neomycin. Of these agents, the cationic antiseptics chlorhexidine and PHMB are generally considered to be the most effective. However, the efficacy of all of these agents in treating *Acanthamoeba* infections is fairly limited. Some of the agents have a limited ability to eradicate *Acanthamoeba*, particularly at the low concentrations required to avoid toxicity to the cornea or other affected tissues, while other agents are inherently toxic to tissues, particularly if prolonged therapy of several weeks or months is required to eradicate the infection.

As with *Acanthamoeba* infections, fungal infections are relatively rare, but are difficult to treat effectively. The difficulty in treating these infections is due to the limited ability of therapeutic agents to eradicate fungi in situ and the toxic effects of most therapeutic agents on the affected tissues or surrounding tissues.

The following publications may be referred to for further background regarding the current therapies for treating *Acanthamoeba* and fungal infections of the cornea and associated ophthalmic tissues:

1. Kosrirukvongs, P., et al., "Treatment of *Acanthamoeba* keratitis with chlorhexidine" *Ophthalmology*, vol. 106 (4), pages 798–802 (1999);
2. Tien, S. H., et al., "Treatment of *Acanthamoeba* keratitis combined with fungal infection with polyhexamethylene biguanide. *Koahsiung J. Med. Sci.*, vol. 15, pages 665–673 (1999);
3. Claerhout, I., et al., "*Acanthamoeba* keratitis: a review" *Bull. Soc. Belge. Ophthalmol.*, vol. 274, pages 71–82 (1999);
4. Lindquist, T. D., "Treatment of *Acanthamoeba* keratitis" *Cornea.*, vol. 17 (1), pages 11–16 (1998);
5. Gatti, S., et al., "In-vitro effectiveness of povidone-iodine on *Acanthamoeba* isolates from human cornea" *Antimicrob. Agents. Chemother*, vol. 42 (9), pages 2232–2234 (1998);
6. Murdoch, D., et al., "*Acanthamoeba* keratitis in New Zealand, including two cases with in-vivo resistance to polyhexamethylene biguanide" *Aust. N. Z. J. Ophthalmol.*, vol. 26 (3), pages 231–236 (1998);
7. Illingworth, C. D., et al., "*Acanthamoeba* keratitis" *Surv. Ophthalmol*, vol. 42 (6), pages 493–508 (1998);
8. Azuara Blanco, A., et al., "Successful medical treatment of *Acanthamoeba* keratitis" *International Ophthalmol.*, vol. 21 (4), pages 223–227 (1998);
9. Duguide, I. G., et al., "Outcome of *acanthamoeba* keratitis treated with polyhexamethyl biguanide and propamidine" *Ophthalmol.*, vol. 104 (10), pages 1587–1592 (1997);
10. Hargrave, S. L., et al., "Results of a trial of combined propamidine isethionate and neomycin therapy of *acanthamoeba* keratitis—Brolene Study Group" *Ophthalmol.*, vol. 106 (5), pages 952–957 (1999);
11. Amoils, S. P., et al., "*Acanthamoeba* keratitis with live isolates treated with cryosurgery and fluconazole" *Am. J. Ophthalmol.*, vol. 127 (6), pages 718–720 (1999);
12. Navarro-Guerrero, J., et al., "Short communications: a case of bilateral *Acanthamoeba* keratitis" *Farm Hosp.*, vol. 22 (5), pages 253–255 (1998);
13. Park, D. H., et al., "The role of topical corticosteroids in the management of *Acanthamoeba* keratitis" *Cornea.*, vol. 16 (3), pages 277–283 (1997);
14. Chung, M. S., et al., "Fungal keratitis after laser in-situ keratomileusis: a case report" *Cornea.*, vol. 19 (2), pages 236–237 (2000);
15. Rodriguez-Ares, T., et al., "Acremonium keratitis in a patient with herpetic neutrotrophic corneal disease" *Acta. Ophthalmol. Scandinavica.*, vol. 78 (1), pages 107–109 (2000);
16. Rahman, M. R., et al., "Trial of chlorhexidine gluconate for fungal corneal ulcers" *Ophthalmic Epidemiol.*, vol. 4 (3), pages 141–149 (1997);

*Acanthamoeba* is a common soil and water amoeba characterized by a feeding and dividing trophozoite and resistant cyst stage. The organism is an opportunistic pathogen of humans, causing a potentially blinding keratitis most frequently seen in contact lens wearers. The resistance of the cyst stage to most antimicrobial agents makes *acanthamoeba* keratitis one of the most difficult ocular infections to manage successfully. Although significant advances in the management of *acanthamoeba* keratitis have been achieved through the use is of polyhexamethylene biguanide and chlorhexidine (0.02% topical application) treatment failures still occur necessitating surgical intervention with penetrating keratoplasty or, ultimately, enucleation.

The above-discussed difficulties in treating ophthalmic infections and associated inflammation attributable to *Acanthamoeba* and fungi are also seen in the treatment of other tissues infected with these microorganisms. This is particularly true with respect to otic and nasal infections.

In view of the foregoing, there is a need for a more effective means of treating *Acanthamoeba* and fungal infections. A therapy that provides for more effective eradication of *Acanthamoeba* and fungi with less potential for toxicity to the infected tissues is particularly needed. The present invention is directed to satisfying these needs.

SUMMARY OF THE INVENTION

The present invention is based on the finding that certain amidoamines are particularly effective in eradicating *Acanthamoeba* and fungi, but are relatively non-toxic to ophthalmic tissues. Based on this finding, the present inventors have succeeded in providing an improved means for treating infections and associated inflammation attributable to *Acanthamoeba* and/or fungi.

The pharmaceutical compositions and methods described herein may be utilized in conjunction with the treatment of various types of *Acanthamoeba* and fungal infections. However, the compositions and methods of the present invention are particularly well-suited for use in treating conditions wherein topical application of the compositions to the affected tissues is possible. The present invention is therefore well suited for topical treatment of ophthalmic, otic and nasal infections, as well as dermatological infections, and is particularly well suited for treating *Acanthamoeba* keratitis.

The compositions of the present invention contain one or more amidoamines described herein, and a pharmaceutically acceptable vehicle therefor. The compositions may also include additional antimicrobial agents to complement or supplement the activity of the amidoamines.

The amidoamines of the present invention offer several advantages relative to the existing therapies for *Acanthamoeba* and fungal infections. For example, these compounds have been found to be effective against strains of *Acanthamoeba* and fungi that are resistant to the current therapeutic agents, such as chlorhexidine. In addition, the amidoamines are effective against *Acanthamoeba* and fungi at concentrations suitable for the topical treatment of ophthalmic tissues and other delicate tissues. This combination of greater microbiocidal activity in combination with less toxicity is believed to represent a significant advancement, relative to the current therapies for *Acanthamoeba* and fungal infections.

DESCRIPTION OF PREFERRED EMBODIMENTS

The amidoamines utilized in the present invention comprise one or more compounds of the following formula, or pharmaceutically acceptable salts thereof (e.g., hydrohalide salts):

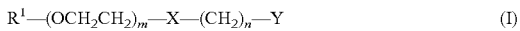

$$R^1—(OCH_2CH_2)_m—X—(CH_2)_n—Y \qquad (I)$$

wherein:

X is 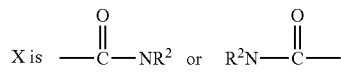

Y is $—N(R^3)_2$ or

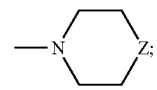

Z is oxygen or $NR^4$;
$R^1$ is $C_6$–$C_{18}$ saturated or unsaturated alkyl, alkylaryl, or alkoxyaryl;
m is zero to 16;
n is 2 to 16;
$R^2$, $R^3$, and $R^4$ are independently hydrogen, $C_1$–$C_8$ saturated or unsaturated alkyl or hydroxyalkyl, or a pharmaceutically acceptable salt thereof.

The compounds wherein m is 0 to 5, n is 2 to 4, $R^2$ is hydrogen or methyl, $R^3$ is methyl or ethyl, and $R^4$ is hydrogen, methyl or hydroxyethyl are particularly preferred, as are the compounds of Table 1, below:

TABLE 1

| COMPD. No. | $R^1$ | M | n | X | $R^2$ | Y | $R^3$ | Z | $R^4$ |
|---|---|---|---|---|---|---|---|---|---|
| 1 | $C_{17}$ | 0 | 3 | $CONR^2$ | H | $N(R^3)_2$ | $CH_3$ | — | — |
| 2 | $C_{13}$ | 0 | 2 | $CONR^2$ | H | $N(R^3)_2$ | $CH_3$ | — | — |
| 3 | $C_{13}$ | 0 | 2 | $CONR^2$ | H | $N(R^3)_2$ | $C_2H_5$ | — | — |
| 4 | $C_{13}$ | 0 | 3 | $CONR^2$ | H | $N(R^3)_2$ | $CH_3$ | — | — |
| 5 | $C_{11}$ | 0 | 3 | $CONR^2$ | H | $N(R^3)_2$ | $CH_3$ | — | — |
| 6 | $C_{11}$ | 0 | 3 | $CONR^2$ | H | $N(R^3)_2$ | $C_2H_5$ | — | — |
| 7 | $C_{11}$ | 0 | 3 | $CONR^2$ | H | (ring) | — | O | — |
| 8 | $C_{14}$ | 0 | 2 | $R^2NCO$ | H | (ring) | — | N | H |
| 9 | $C_{13}$ | 0 | 3 | $CONR^2$ | H | (ring) | — | N | $CH_3$ |
| 10 | $C_{13}$ | 0 | 3 | $CONR^2$ | $CH_3$ | $N(R^3)_2$ | $CH_3$ | — | — |
| 11 | $C_{13}$ | 0 | 3 | $CONR^2$ | H | (ring) | — | N | $C_2H_4OH$ |
| 12 | $C_{12}$ | 5 | 3 | $CONR^2$ | H | $N(R^3)_2$ | $CH_3$ | — | — |
| 13 | $C_{12}$ | 4 | 2 | $R^2NCO$ | H | $N(R^3)_2$ | $CH_3$ | — | — |
| 14 | $C_{12}$ | 0 | 3 | $CONR^2$ | H | $N(R^3)_2$ | $CH_3$ | — | — |
| 15 | $C_{11}$ | 0 | 3 | $CONR^2$ | $CH_3$ | $N(R^3)_2$ | $CH_3$ | — | — |

TABLE 1-continued

| COMPD. No. | $R^1$ | M | n | X | $R^2$ | Y | $R^3$ | Z | $R^4$ |
|---|---|---|---|---|---|---|---|---|---|
| 16 | $C_{11}$ | 0 | 3 | $CONR^2$ | H | (piperazine ring N—Z) | — | N | $C_2H_4OH$ |
| 17 | $C_{13}$ | 0 | 3 | $CONR^2$ | H | (piperazine ring N—Z) | — | O | — |

The most preferred amidoamine is Compound No. 4, which is known as N,N-Dimethyl-N'-tetradecanoyl-1,3-propylenediamine or N-[3-(Dimethylamino)propyl] tetradecanamide. This compound may also be referred to as "CAS Number: 45267-19-4".

Some of the amidoamines utilized in the present invention are available from commercial sources. For example, Compound No. 4 is available as MIRISTOCOR®, myristamidopropyl dimethylamine phosphate, from Hoffman-La Roche Inc., Nutley, N.J. (USA), and as Schercodine M from Scher Chemicals Inc., Clifton, N.J. (USA); Compound No. 5 is available as LEXAMINE® L-13, lauramidopropyl dimethylamine, from Inolex Chemical Company, Philadelphia, Pa. (USA); and Compound No. 1 is available as LEXAMINE® S-13, stearamidopropyl dimethylamine, also from Inolex Chemical Company.

The above-described amidoamines can be synthesized in accordance with known techniques, including those described in U.S. Pat. No. 5,573,726 (Dassanayake, et al.), the entire contents of which are hereby incorporated in the present specification by reference. Examples of general reaction schemes which may be utilized are provided below.

Scheme I

The following reaction scheme may be utilized to synthesize compounds wherein

X is $CONR^2$:

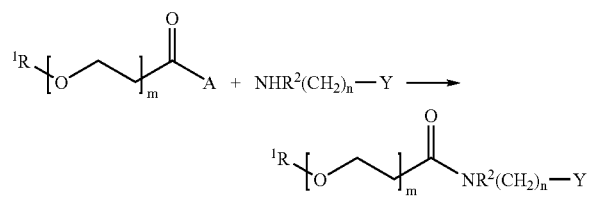

In the foregoing reaction scheme, A is a good leaving group, such as chloride or N-hydroxysuccinimide.

Scheme II

The following reaction scheme may be utilized to synthesize compounds wherein

X is $NR^2CO$

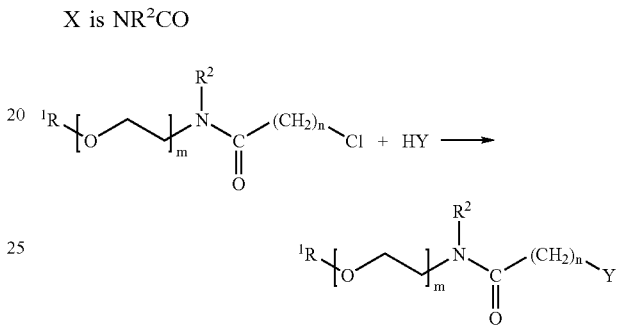

The following article may be referred to for further details concerning the synthesis of the amidoamines of formula (I): Muzyczko, et al., "Fatty Amidoamine Derivatives: N,N-Dimethyl-N-(3-alkylamidopropyl)amines and Their Salts", *Journal of the American Oil Chemists' Society*, volume 45, number 11, pages 720–725 (1968).

The amidoamines of formula (I) can be used individually, in combination with one or more other compounds of formula (I), or in combination with other antimicrobial agents. The compounds may, for example, be used in combination with cationic antiseptics, aminoglycoside antibiotics, quinolone antibiotics, oxazolidinone antibiotics or tetracycline. Examples of suitable cationic antiseptics include biguanides, such as chlorhexidine and polyhexamethylene biguanide ("PHMB"), and quaternary-ammonium compounds, such as benzalkonium chloride and polyquaternium-1.

The compositions of the present invention may also contain one or more low molecular weight amino alcohols to further enhance the antimicrobial activity of the compositions. The preferred amino alcohol is 2-amino-2-methylpropanol ("AMP"). The term "AMP 95" refers to a commercially available solution (Angus Chemical Company, Buffalo Grove, Ill.) that contains 95% pure AMP and 5% water. AMP 95 is the most preferred low molecular weight amino alcohol.

The amount of the amidoamines of formula (I) utilized in the compositions of the present invention will depend on the purpose of the use, e.g., the treatment of an active infection or the prophylactic treatment of tissues to prevent an active infection from developing. The amount utilized will also depend on the particular tissues being treated. For example, lower concentrations will typically be utilized to treat especially sensitive tissues, such as ophthalmic tissues, while somewhat higher concentrations may be utilized to treat less sensitive tissues, such as the skin. The amount of amidoamine utilized will also depend on the presence or absence of other antimicrobial agents in the present compositions. The concentrations determined to be necessary for the above-stated purposes can be functionally described as "an antiinfective amount", "an antimicrobial effective amount" or variations thereof. The concentrations utilized will generally be in the range of from about 0.00001 to about 0.1 weight/volume percent (w/v %).

The amidoamines of formula (I) may be included in various types of pharmaceutical compositions. The compositions may be aqueous or nonaqueous, but will generally be aqueous. As will be appreciated by those skilled in the art, the compositions may contain a wide variety of ingredients, such as tonicity agents (e.g., sodium chloride or mannitol), surfactants (e.g., polyoxyethylene/polyoxypropylene copolymers, such as Poloxamine™), viscosity adjusting agents (e.g., hydroxypropyl methyl cellulose and other cellulose derivatives) and buffering agents (e.g., borates, citrates, phosphates and carbonates). The inclusion of borate and/or one or more surfactants in the compositions has been found to enhance the overall antimicrobial activity of the compositions. The inclusion of such agents is therefore desirable in most cases.

It has been found that the amidoamines of formula (I) are most active under alkaline conditions. Accordingly, the compositions of the present invention will preferably be formulated to have a pH greater than 7. The ideal pH values for compositions containing specific amidoamines of formula (I) can be determined by means of routine experimentation, but these values will generally be in the range of 7.5 to 8.0.

As will be appreciated by those skilled in the art, ophthalmic compositions intended for direct application to the eye will be formulated so as to have a pH and tonicity which are compatible with the eye. This will normally require a buffer to maintain the pH of the composition at or near physiologic pH (i.e., 7.4) and may require a tonicity agent to bring the osmolality of the composition near to 300 milliosmoles. However, as indicated above, a slightly alkaline pH is preferred in order to maximize the antimicrobial effect of the amidoamines of formula (I).

The compositions of the present inventions are preferably utilized to treat *Acanthamoeba* and fungal infections by applying the compositions to the affected tissues from a few to several times per day. The amount of composition applied and the frequency of application are dependent on the particular type of tissue being treated and the severity of the infection.

The following examples are presented to further illustrate methods of synthesizing the amidoamines of formula (I), pharmaceutical compositions containing these compounds, and the antimicrobial activity of these compounds relative to *Acanthamoeba* and fungi.

EXAMPLE 1

Synthesis of Compound No. 4 (N,N-Dimethyl-N'-Tetradecanoyl-1,3-Propylenediamine)

2.0 g. (0.0196 moles) of 3-dimethylaminopropylamine in 40 ml chloroform was added dropwise to an ice cold chloroform solution (50 ml) of myristoyl chloride (4.17 g., 0.0169 moles). After addition, the ice bath was removed and the solution was stirred for 2 hours. A 25 ml aqueous sodium bicarbonate solution was added and stirred for 30 minutes. The organic layer was then washed with 30 ml aqueous sodium bicarbonate/sodium chloride solution and dried with magnesium sulfate. The solution was concentrated in vacuo and the amide was recrystallized in ethyl acetate to yield 3.29 g. (0.0105 moles, 62.3%) of the subject compound.

$^1$H NMR (200 MHz, CDCL$_3$): δ6.9 (s, 1H, NH), 3.3 (q, 3H, NHC$\underline{H}_2$), 2.4 (t, 2H, NCH$_2$), 2.22 (s, 6H, NCH$_3$), 2.15 (t, 2H, COCH$_2$), 1.7–1.5 (m, 4H, COCH$_2$C$\underline{H}_2$ and NHCH$_2$C$\underline{H}_2$), 1.25 (s, 20H, COCH$_2$CH$_2$(C$\underline{H}_2$)$_{10}$), 0.88 (t, 3H, CH$_3$). Elemental Analysis: Calculated for C$_{19}$H$_{40}$N$_2$O (312.52): C, 73.02; H, 12.90; N, 8.96. Found: C, 72.96; H, 12.92; N, 8.93.

EXAMPLE 2

The following formulations are examples of aqueous compositions containing the amidoamines of formula (I). The formulations are suitable for topical application to the eye and other tissues.

| Ingredient | Amount (w/v %) |
|---|---|
| Formulation No. 1 | |
| Compound No. 4 | 0.001 to 0.01 |
| Boric Acid | 0.3 |
| Sodium Chloride | 0.64 |
| NaOH/HCL | q.s. pH 7.8 |
| Purified Water | q.s. 100 |
| Formulation No. 2 | |
| Compound No. 4 | 0.005 |
| Sodium Chloride | 0.5 |
| Mannitol | 2.5 |
| HEPES | 0.119 |
| NaOH/HCl | q.s. pH 7.0 |
| Purified water | q.s. 100 |
| Formulation No. 3 | |
| Compound No. 4 | 0.001 |
| Boric Acid | 0.58 |
| Sodium Borate | 0.18 |
| Sodium Chloride | 0.49 |
| Disodium Edetate | 0.05 |
| NaOH/HCl | q.s. pH 7.0 |
| Purified water | q.s. 100 |
| Formulation No. 4 | |
| Compound No. 4 | 0.0005 |
| AMP 95 | 0.45 |
| Boric Acid | 0.6 |
| Disodium Edetate | 0.05 |
| Sodium Chloride | 0.1 |
| Sodium Citrate | 0.65 |
| Sorbitol | 1.2 |
| Tetronic 1304 | 0.05 |
| NaOH/HCl | q.s. pH 7.8 |
| Purified water | q.s. |

EXAMPLE 3

The following experiment was conducted to evaluate the activity of the amidoamines of formula (I) against *Acanthamoeba*.

A 0.1% stock solution of Compound No. 4 was prepared. The compound was dissolved in TRIS buffer[1] by gently heating and swirling. The final pH was adjusted to 7.8 with 1N HCl. The TRIS buffer control showed that growth of *Acanthamoeba* was not inhibited by the TRIS. To prepare the samples, a 0.1% stock solution of Compound No. 4 was serially diluted in Mueller Hinton Broth (MHB)[2,3] (BBL) to provide concentrations of 0.01 w/v %, 0.001 w/v %, 0.0001 w/v %, and 0.00001 w/v %, respectively. Solutions containing 0.02 w/v % polyhexamethylene biguanide (PHMP) and 0.1 w/v % chlorhexidine, respectively, were also utilized as controls.

The samples were inoculated with low levels (approximately 3.0×10² organisms/mL) of the test organism. The test organism was *Acanthamoeba polyphaga* cysts (ATCC 30871) produced 14 days in. PYG and then 14 days in Page's saline, followed by one month of refrigeration. The samples were checked for survivors at 4, 24, and 48 hours post inoculation. The samples were serially diluted in Dey-Engley neutralizing broth (DE) (Difco) and plated in quadruplicate in tissue culture plate wells containing non-nutrient agar overlaid with *E. coli*. Plates were sealed and incubated for 14 days at 30–35° C. Results were recorded and counts calculated using the Reed and Muench computation. The results are set forth in Table 2 below:

1N HCl. The TRIS buffer control showed that growth of the fungi was not inhibited by the TRIS. To prepare the samples, a 0.1% stock solution of Compound No. 4 was serially diluted in Mueller Hinton Broth (MHB)[2,3] (BBL) to provide solutions containing Compound No. 4 in concentrations of 0.01 w/v %, 0.001 w/v %, 0.0001 w/v %, and 0.00001 w/v %, respectively. Solutions containing 0.02 w/v % PHMB and 0.1 w/v % chlorhexidine, respectively, were utilized as controls.

The samples were inoculated with low levels (approximately 1.0×10³ organisms/mL) of the test organism. The test organisms included the fungi *C. albicans* ATCC

TABLE 2

Dose/Response Data for Compound No. 4 Against Acanthamoeba

| | | Number of Surviving Organisms | | | | | |
|---|---|---|---|---|---|---|---|
| Organism | Time (Hrs) | 0.01% Compound No. 4 | 0.001% Compound No. 4 | 0.0001% Compound No. 4 | 0.00001% Compound No. 4 | 0.02% PHMB | 0.1% Chlorhexidine |
| *A. polyphaga* | 0 | $3.2 \times 10^2$ | $3.2 \times 10^2$ | $3.2 \times 10^2$ | $3.2 \times 10^2$ | $3.2 \times 10^2$ | $3.2 \times 10^2$ |
| ATCC | 4 | <10 | $3.2 \times 10^2$ | $3.2 \times 10^3$ | $3.2 \times 10^3$ | <10 | <10 |
| 30871 | 24 | <10 | $1.7 \times 10^1$ | $2.1 \times 10^3$ | $3.2 \times 10^3$ | <10 | <10 |
| Cysts | 48 | <10 | <10 | $2.1 \times 10^3$ | $3.2 \times 10^3$ | <10 | <10 |

[1]TRIS buffer was made in sterile water as follows: TRIS (12.11 g/L) and NaCl (8 g/L); add 1.0 N HCL to pH 7.8.
[2]MHB was made in phosphate buffered saline [NaCl (8.3 g/L), sodium phosphate dibasic (2.38 g/L), sodium phosphate monobasic (0.467 g/L), in distilled water].
[3]MHB is recommended as the medium of choice by the National Committee for Clinical Laboratory Standards (NCCLS) M7-A5, Vol. 20, No. 2, pg. 10) for susceptibility testing of commonly isolated, rapidly growing organisms.

EXAMPLE 4

The following experiment was conducted to evaluate the activity of the amidoamines of formula (1) against fungi.

A 0.1% stock solution of Compound No. 4 was prepared. The compound was dissolved in TRIS buffer[1] by gently heating and swirling. The final pH was adjusted to 7.8 with 10231 and *F. solani* ATCC 36031. The samples were checked for survivors at 4, 24, and 48 hours post inoculation. The samples were serially diluted in Dey Engley neutralizing broth (DE) (Difco) and plated in duplicate using trypicase soy agar containing 0.07% asolectin and 0.5% Tween 80. The plates were incubated for 5 days at 20–25° C. and plate counts recorded. The results are set forth in Table 3, below.

TABLE 3

Dose/Response Data for Compound No. 4 Against Fungi

| | | Number of Surviving Organisms | | | | | |
|---|---|---|---|---|---|---|---|
| Organism | Time (Hours) | 0.01% Compound No. 4 | 0.001% Compound No. 4 | 0.0001% Compound No. 4 | 0.00001% Compound No. 4 | 0.02% PHMB | 0.1% Chlorhexidine |
| *C. albicans* | 0 | $3.3 \times 10^3$ | $3.3 \times 10^3$ | $3.3 \times 10^3$ | $3.3 \times 10^3$ | $3.3 \times 10^3$ | $3.3 \times 10^3$ |
| ATCC | 4 | <1 | $4.3 \times 10^1$ | $3.2 \times 10^3$ | $3.2 \times 10^3$ | <1 | <1 |
| 10231 | 24 | <1 | $1.0 \times 10^1$ | $1.5 \times 10^4$ | $2.5 \times 10^4$ | <1 | <1 |
| | 48 | <1 | $3.4 \times 10^1$ | $1.3 \times 10^5$ | $1.3 \times 10^5$ | <1 | <1 |
| *F. solani* | 0 | $4.9 \times 10^3$ | $4.9 \times 10^3$ | $4.9 \times 10^3$ | $4.9 \times 10^3$ | $4.9 \times 10^3$ | $4.9 \times 10^3$ |
| ATCC | 4 | <1 | $1.0 \times 10^1$ | $6.9 \times 10^3$ | $5.9 \times 10^3$ | <1 | <1 |
| 36031 | 24 | <1 | <1 | $9.5 \times 10^3$ | $1.0 \times 10^4$ | <1 | <1 |
| | 48 | <1 | <1 | $1.6 \times 10^4$ | $4.8 \times 10^3$ | <1 | <1 |

[1]TRIS buffer was made in sterile water as follows TRIS (12.11 g/L) and NaCl (8 g/L); add 1.0 N HCL to pH 7.8.
[2]MHB was made in phosphate buffered saline [NaCl (8.3 g/L), sodium phosphate dibasic (2.38 g/L), sodium phosphate monobasic (0.467 g/L), in distilled water].
[3]MHB is recommended as the medium of choice by the National Committee for Clinical Laboratory Standards (NCCLS) M7-A5, Vol. 20, No. 2, pg. 10) for susceptibility testing of commonly isolated, rapidly growing organisms.

EXAMPLE 5

The following experiment was conducted to determine the minimum cysticidal concentration ("MCC") of Compound No. 4 against five strains of *Acanthamoeba*, and compare the MCC values for Compound No. 4 to those for chlorhexidine.

Two different vehicles were utilized to prepare solutions containing Compound No. 4. The first vehicle was the same as the vehicle described in Formulation No. 4 (see Example 2, above), and the second vehicle was a 2 mM TRIS. HCl solution (pH 7.8).

Minimum cysticidal levels of Compound No. 4 for *Acanthamoeba* keratitis strains was determined as follows. Briefly, 100 µl serial, two-fold dilutions were prepared across the rows of a microtitre plate. Control wells received only diluent. An equal volume of five strains of *Acanthamoba* cysts were added to the wells and the plates sealed and incubated at 32° C. for 24 hours. Using a multi-channel pipette, the solutions in the wells were removed and replaced with 200 µl of ¼ strength Lactated Ringer's solution and left at room temperature for 15 minutes. The washing procedure was repeated twice more before finally filling the wells with 100 µl of ¼ strength Lactated Ringer's solution containing live *E. coli* at an O.D.$_{540}$ of 0.2. The plates were then sealed and incubated at 32° C. for up to 7 days. The minimum cysticidal concentration (MCC) was defined as the lowest concentration of antimicrobial solution that resulted in no excystment and trophozoite replication.

The MCC values for Compound No. 4 and chlorhexidine against the five *Acanthamoeba* strains (NNA cysts) tested are set forth in Table 4, below.

TABLE 4

| | Minimum Cysticidal Concentration (micrograms/milliliter) | | | | |
|---|---|---|---|---|---|
| Formulation | Acanthamoeba Strain 1501-3D | Acanthamoeba Strain Uni Tap Water 1501-3D | Acanthamoeba Strain 1501-2g | Acanthamoeba Strain Ros | Acanthamoeba Strain Watson |
| ALDOX in Tris Buffer | 15.6 | 15.6 | 13.0 | 15.6 | 31.3 |
| ALDOX in Vehicle | 22.5 | 22.5 | 11.3 | 15.6 | 31.3 |
| Chlorhexidine | 31.3 | 26.0 | 52.1 | 31.25 | 62.5 |

EXAMPLE 6

The efficacy of a formulation containing 0.0005% of Compound No. 4 was tested against several species of both yeast and mold. (The formulation tested was OPTI-FREE® Express® Multi-Purpose Disinfecting Solution, which is identical to Formulation No. 4 in Example 2 above, expect that the OPTI-FREE® Express Solution also contains polyquaternium-1 in a concentration of 0.001 w/v %.) The formulation was inoculated to contain approximately 1×10$^6$ CFU/ml of the inoculum. Samples were serially diluted in Dey-Engley medium and plated in soybean-casein digest agar containing neutralizers. The plates were incubated and the numbers of survivors were recorded. The average reduction for mold was 2.9-log units and yeasts were reduced by an average of 3.9-log units after 6-hours of exposure to the formulation. The test results are presented in Table 5 below.

TABLE 5

Efficacy Against Fungi—Log Reduction at 6 Hours

| Microorganism | Average Log Reduction | SD | N |
|---|---|---|---|
| *Candida parapsilosis* | 5.00 | ±0.0 | 3 |
| *Candida albicans* 2 | 2.19 | ±0.7 | 16 |
| *Candida albicans* 1* | 4.53 | ±0.3 | 3 |
| *Penicillium notatum* | 2.33 | ±0.8 | 3 |
| *Paecilomyces lilacinus* | 2.70 | ±0.1 | 3 |
| *Fusarium solani* | 4.19 | ±0.8 | 9 |
| *Curvularia clavata* | 1.37 | ±0.3 | 3 |
| *Aspergillus fumigatus* | 3.10 | ±1.0 | 3 |

What is claimed is:

1. A method of treating infections attributable to *Acanthamoeba*, fungi or a combination of *Acanthamoeba* and fungi, which comprises applying a topical pharmaceutical composition to the affected tissues, said composition comprising an antimicrobial effective amount of a compound of the following formula:

$$R^1—(OCH_2CH_2)_m—X—(CH_2)_n—Y \qquad (I)$$

wherein:

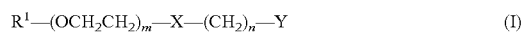

X is $-\overset{O}{\underset{\|}{C}}-NR^2$ or $R^2N-\overset{O}{\underset{\|}{C}}-$ ;

Y is $—N(R^3)_2$ or

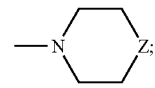

Z is oxygen or NR$^4$;
R$^1$ is C$_6$–C$_{18}$ saturated or unsaturated alkyl, alkylaryl, or alkoxyaryl;
m is zero to 16;
n is 2 to 16;
R$^2$, R$^3$, and R$^4$ are independently hydrogen, C$_1$–C$_8$ saturated or unsaturated alkyl or hydroxyalkyl, or a pharmaceutically acceptable salt thereof; and
a pharmaceutically acceptable vehicle therefor.

2. A method according to claim 1, wherein n is 2 to 4, and m is 0 to 5.

3. A method according to claim 2, wherein R$^2$ is hydrogen or methyl, and R$^3$ is methyl or ethyl.

4. A method according to claim 1, wherein R$^1$ is heptadec-8-enyl, undecyl, undecenyl, dodecyl, tridecyl, tetradecyl, pentadecyl or heptadecyl, $R^2$ is hydrogen or methyl, $R^3$ is methyl or ethyl, and $R^4$ is hydrogen, methyl or hydroxyethyl.

5. A method according to claim 1, wherein $R^1$ is tridecyl, m is 0, n is 3, Y is $N(R^3)_2$ and $R^3$ is methyl.

6. A method according to claim 1, wherein the composition further comprises an antimicrobial effective amount of a cationic antiseptic.

7. A method according to claim 6, wherein the cationic antiseptic is selected from the group consisting of chlorhexidine, PHMB and polyquaternium-1.

8. A method according to claim 1, wherein the composition is applied to ophthalmic tissues.

9. A method according to claim 1, wherein the composition is applied to ophthalmic tissues to treat an *Acanthamoeba* infection.

10. A method according to claim 5, wherein the composition is applied to ophthalmic tissues.

11. A method according to claim 5, wherein the composition is applied to ophthalmic tissues to treat an *Acanthamoeba* infection.

* * * * *